US009944751B2

(12) United States Patent
Pinnau et al.

(10) Patent No.: US 9,944,751 B2
(45) Date of Patent: Apr. 17, 2018

(54) TRIPTYCENE-BASED LADDER MONOMERS AND POLYMERS, METHODS OF MAKING EACH, AND METHODS OF USE

(71) Applicant: KING ABDULLAH UNIVERSITY OF SCIENCE AND TECHNOLOGY, Thuwal (SA)

(72) Inventors: Ingo Pinnau, Thuwal (SA); Bader Ghanem, Thuwal (SA); Raja Swaidan, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 4 days.

(21) Appl. No.: 14/907,924

(22) PCT Filed: Jul. 23, 2014

(86) PCT No.: PCT/IB2014/001742
§ 371 (c)(1),
(2) Date: Jan. 27, 2016

(87) PCT Pub. No.: WO2015/015299
PCT Pub. Date: Feb. 5, 2015

(65) Prior Publication Data
US 2016/0168325 A1 Jun. 16, 2016

Related U.S. Application Data

(60) Provisional application No. 61/859,800, filed on Jul. 30, 2013.

(51) Int. Cl.
| | |
|---|---|
| *B01D 53/22* | (2006.01) |
| *C08G 65/38* | (2006.01) |
| *B01D 71/62* | (2006.01) |
| *C07D 241/38* | (2006.01) |
| *C08G 73/06* | (2006.01) |
| *B01D 69/02* | (2006.01) |
| *C08G 65/40* | (2006.01) |
| *B01D 67/00* | (2006.01) |

(52) U.S. Cl.
CPC ............ *C08G 65/38* (2013.01); *B01D 53/22* (2013.01); *B01D 53/228* (2013.01); *B01D 69/02* (2013.01); *B01D 71/62* (2013.01); *C07D 241/38* (2013.01); *C08G 65/4075* (2013.01); *C08G 73/0694* (2013.01); *B01D 67/0013* (2013.01); *B01D 2256/10* (2013.01); *B01D 2256/245* (2013.01); *B01D 2257/104* (2013.01); *B01D 2257/108* (2013.01); *B01D 2257/504* (2013.01); *B01D 2325/00* (2013.01); *Y02C 10/10* (2013.01); *Y02P 20/152* (2015.11)

(58) Field of Classification Search
CPC .. B01D 53/22; B01D 53/228; B01D 67/0013; B01D 69/02; B01D 71/62; B01D 2256/10; B01D 2256/245; B01D 2257/104; B01D 2257/108; B01D 2257/504; B01D 2325/00; C08G 65/38; C08G 65/4075; C08G 73/0694; C07D 241/38
See application file for complete search history.

(56) References Cited

U.S. PATENT DOCUMENTS

| | | | | | |
|---|---|---|---|---|---|
| 3,542,734 | A | * | 11/1970 | Rippie | C08G 18/3215 528/183 |
| 6,605,693 | B1 | * | 8/2003 | Becker | C07C 17/14 257/40 |
| 2006/0246273 | A1 | * | 11/2006 | McKeown | B01D 53/228 428/314.8 |
| 2008/0039455 | A1 | * | 2/2008 | Ince | C07D 487/04 514/233.2 |
| 2009/0043068 | A1 | * | 2/2009 | Capehart | C08G 65/40 528/171 |
| 2010/0130634 | A1 | * | 5/2010 | Fritsch | B01J 19/0093 521/189 |
| 2016/0102177 | A1 | * | 4/2016 | Ghanem | B01D 71/64 95/47 |

OTHER PUBLICATIONS

Ghanem, Bader S., "A facile synthesis of a novel triptycene-containing A-B monomer: precursor to polymers of intrinsic microporosity", Polymer Chemistry, Oct. 2011, 3, pp. 96-98.*
Ghanem, Bader S. et al., "Triptycene-Based Polymers of Intrinsic Microporosity: Organic Materials That Can be Tailored for Gas Adsorption", Macromolecules, Jun. 2010, 43, pp. 5287-5294.*
International Search Report and Written Opinion of Application No. PCT/IB2014/001742 dated Dec. 22, 2014, (11 pages).
Bader S. Ghanem, "A facile synthesis of a novel triptycene-containing A-B monomer: precursor to polymers of intrinsic microporosity", Polymer Chemistry, vol. 3, No. 1; Oct. 26, 2011, pp. 96-98.
Bader S. Ghanem et al., "Triptycene-Based Polymers of Intrinsic Microporosity: Organic Materials That Can Be Tailored for Gas Adsorption", Macromolecules, vol. 43, No. 12, Jun. 22, 2010, pp. 5287-5294.
Budd P.M. et al., "Gas separation membranes from polymers of intrinsic microporosity", Journal of Membrane Science, Elsevier, vol. 251, No. 1-2, Feb. 15, 2005, pp. 263-269.
Bader S. Ghanem et al., "Energy-Efficient Hydrogen Separation by AB-Type Ladder-Polymer Molecular Sieves", Advanced Materials, vol. 26, No. 39, Jul. 19, 2014, pp. 6696-6700.

* cited by examiner

*Primary Examiner* — Jason M Greene
(74) *Attorney, Agent, or Firm* — Billion & Armitage; Benjamin C. Armitage

(57) ABSTRACT

Embodiments of the present disclosure provide for a triptycene-based A-B monomer, a method of making a triptycene-based A-B monomer, a triptycene-based ladder polymer, a method of making a triptycene-based ladder polymers, a method of using triptycene-based ladder polymers, a structure incorporating triptycene-based ladder polymers, a method of gas separation, and the like.

13 Claims, No Drawings

TRIPTYCENE-BASED LADDER MONOMERS AND POLYMERS, METHODS OF MAKING EACH, AND METHODS OF USE

CROSS-REFERENCE TO RELATED APPLICATIONS

This application is the National Stage of International Application No. PCT/IB2014/001742, filed 23 Jul. 2014, which claims the benefit of and priority to U.S. Provisional Application No. 61/859,800, filed on 30 Jul. 2013, having the title "TRIPTYCENE-BASED LADDER MONOMERS AND POLYMERS, METHODS OF MAKING EACH, AND METHODS OF USE", the contents of all of which are incorporated by reference as if fully set forth herein.

BACKGROUND

Gas separation is an emerging technology with a rapidly developing market comprising applications like air separation for oxygen or nitrogen enrichment as well as acid gas removal and hydrocarbon recovery from natural gas streams. The economics of a membrane-based separation system depend on the gas permeability (thickness- and pressure-normalized flux) and selectivity (preferential permeation of one gas over another) of the material used. Unfortunately, there is a conventional trade-off between these two main parameters such that an increase in permeability is concurrent with a decrease in selectivity, and vice versa. This results in what is commonly referred to as an "upper-bound" to performance which is defined by polymeric materials with the highest known combinations of permeability and selectivity. It is revised to accommodate discoveries of better performing polymers and is therefore taken as a gauge of the state-of-the-art.

Strong research efforts in academia and industry are currently invested towards increasing the permeability of polymeric membranes without compromising selectivity by introducing microporosity, considered by the International Union of Pure and Applied Chemistry (IUPAC) to encompass pores less than 20 Å. A conventional technique to introduce microporosity into polymers is thermal treatment. However, this adds complexity to the membrane formation process and often results in insoluble, brittle films. Recently, a British group designed polymers with repeat units comprising a site of contortion in a rigid, wholly-fused ring backbone where there are no single-bonds about which free rotation can occur. This results in inefficient packing of chains in the solid state, trapping free volume and thus generating microporosity inherent to the polymer. These so-called polymers of intrinsic microporosity (PIMs) typically demonstrate high internal surface area, high thermal stability and, very importantly, high solubility in common organic solvents (key to forming membranes for gas separation applications) and amenability to functionalization (permitting tuning of performance for chemically interacting penetrant molecules). To date, ladder-type PIMs are conventionally prepared with a tetrahedral, spiro-carbon center by polycondensation between a bifunctional hydroxylated aromatic monomer (AA) and an activated fluorinated or chlorinated monomer (BB) to form dibenzodioxane-linking groups. Regarding gas separation performance, PIMs have found great success in producing significantly higher gas permeabilities than commercial polymeric membrane materials, but at the expense of selectivity. Therefore, commercial use has been severely hindered for important gas separation applications, such as $O_2/N_2$, $CO_2/CH_4$, $H_2/CH_4$ and others.

SUMMARY

Embodiments of the present disclosure provide for a triptycene-based A-B monomer, a method of making a triptycene-based A-B monomer, a triptycene-based ladder polymer, a method of making a triptycene-based ladder polymer, a method of using triptycene-based ladder polymer, a structure incorporating triptycene-based ladder polymers, a method of gas separation, and the like.

An embodiment of the present disclosure includes a composition, among others, that includes: a triptycene-based ladder polymer having the following structure:

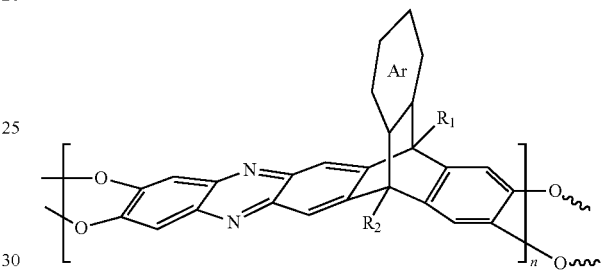

wherein n is 1 to 10,000, wherein Ar is a substituted or un-substituted aromatic moiety, wherein each of R1 and R2 is independently selected from the group consisting of: hydrogen, a halogen, a substituted or un-substituted, branched or linear alkyl group, a substituted or un-substituted aryl group, a substituted or un-substituted heteroaryl group, and substituted or un-substituted phenyl group. In an embodiment, the triptycene-based ladder polymer can have one of the following structures:

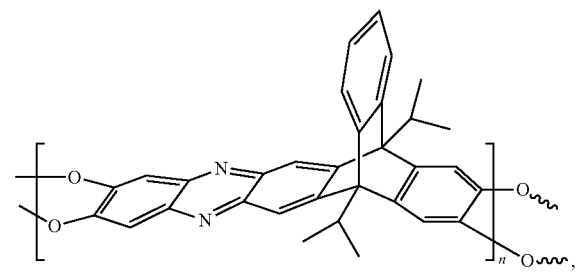

,

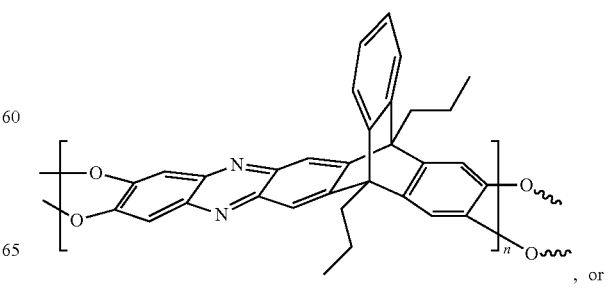

, or

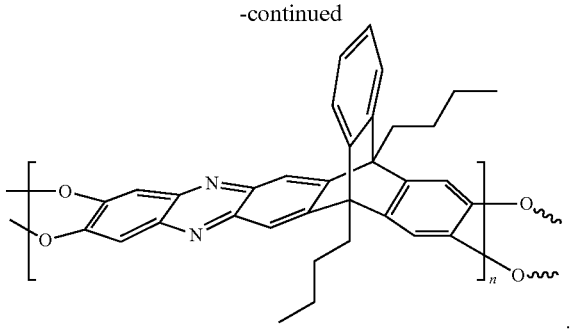

An embodiment of the present disclosure includes a composition, among others, that includes: a monomer described by the following structure:

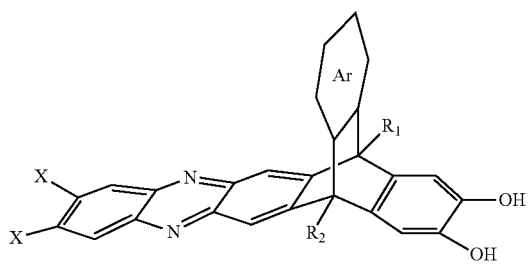

wherein Ar is a substituted or un-substituted aromatic moiety, wherein each of R1 and R2 is independently selected from the group consisting of: hydrogen, a substituted or un-substituted, linear or branched alkyl group, a substituted or un-substituted aryl group, a substituted or un-substituted heteroaryl group, and substituted or un-substituted phenyl group, and wherein X is a halogen.

An embodiment of the present disclosure includes a method of making a monomer, among others, that includes:

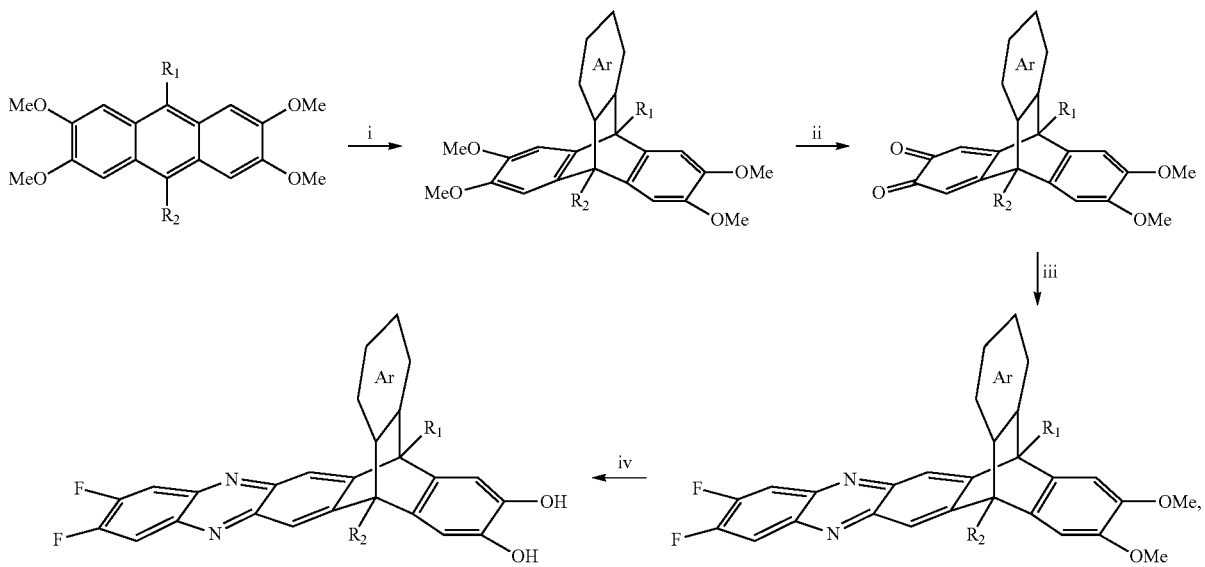

wherein Ar is a substituted or un-substituted aromatic moiety, wherein each of R1 and R2 is independently selected from the group consisting of: hydrogen, a substituted or un-substituted, linear or branched alkyl group, a substituted or un-substituted aryl group, a substituted or un-substituted heteroaryl group, and substituted or un-substituted phenyl group, wherein: step (i) includes a diazonium salt of anthranilic acid or substituted anthranilic acid, 1,2-epoxypropane, $CH_2Cl_2$, reflux; step (ii) includes 0.25 M $HNO_3$, AcOH and $CH_2Cl_2$ (1:1, v:v); step (iii) includes 4,5-difluoro-1,2-diaminobenzene, ethanol, reflux; and step (iv) includes $BBr_3$, $CH_2Cl_2$.

An embodiment of the present disclosure includes a method of making a triptycene-based ladder polymer, among others, that includes:

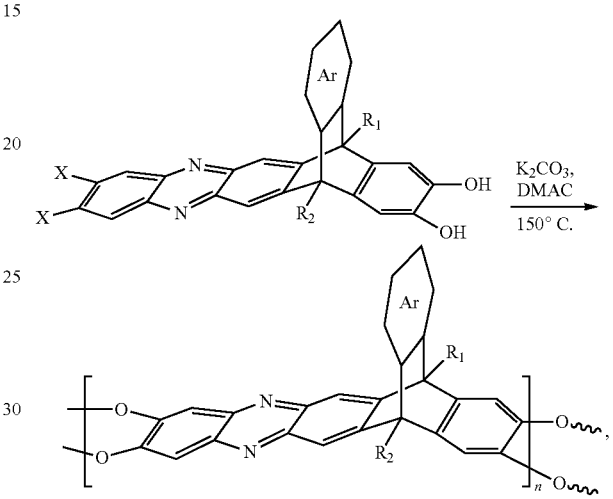

wherein Ar is a substituted or un-substituted aromatic moiety, wherein each of R1 and R2 is independently selected from the group consisting of: hydrogen, a substituted or un-substituted, linear or branched alkyl group, a substituted or un-substituted aryl group, a substituted or un-substituted heteroaryl group, and substituted or un-substituted phenyl group, and wherein X is a halogen.

An embodiment of the present disclosure includes a membrane, among others, that includes: a polymer including a triptycene-based ladder polymer having the following structure:

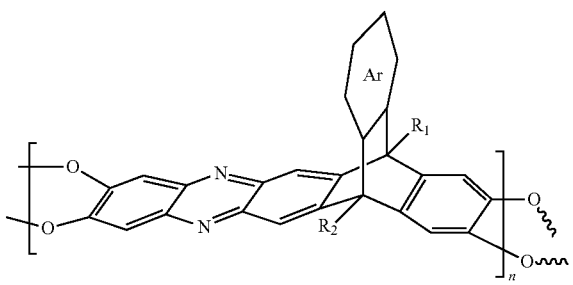

wherein n is 1 to 10,000, wherein Ar is a substituted or un-substituted aromatic moiety, wherein each of R1 and R2 is independently selected from the group consisting of: hydrogen, a halogen, a substituted or un-substituted, branched or linear alkyl group, a substituted or un-substituted aryl group, a substituted or un-substituted heteroaryl group, and substituted or un-substituted phenyl group.

An embodiment of the present disclosure includes a method of separating a gas from a gas mixture, among others, that includes: separating a first gas from a first gas mixture with a membrane to form a second gas mixture, wherein the membrane includes a polymer including a triptycene-based ladder polymer having the following structure:

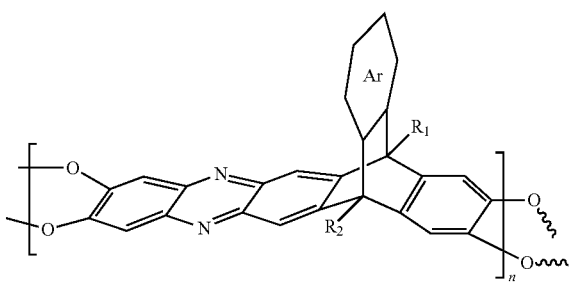

wherein n is 1 to 10,000, wherein Ar is a substituted or un-substituted aromatic moiety, wherein each of R1 and R2 is independently selected from the group consisting of: hydrogen, a halogen, a substituted or un-substituted, branched or linear alkyl group, a substituted or un-substituted aryl group, a substituted or un-substituted heteroaryl group, and substituted or un-substituted phenyl group.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, polymer chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "substituted" refers to any one or more hydrogens on the designated atom that can be replaced with a selection from the indicated group, provided that the designated atom's normal valence is not exceeded.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkyl, alkenyl, and alkynyl groups, and alkanes, alkene, and alkynes, for example.

As used herein, "cyclic" group refers to a cyclic hydrocarbon having a stable 4, 5, 6, 7, 8, 9, 10, 11, or 12 membered (e.g., carbon or hetero), (unless the number of members is otherwise recited), monocyclic, bicyclic, or tricyclic cyclic ring.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, sec-butyl, t-butyl, n-pentyl, isopentyl and sec-pentyl. The term "lower alkyl" means an alkyl group having less than 10 carbon atoms.

The term "substituted," as in "substituted alkyl", "substituted aryl," "substituted heteroaryl" and the like means that the substituted group may contain in place of one or more hydrogens a group such as alkyl, hydroxy, amino, halo, trifluoromethyl, cyano, —NH(alkyl), —N(alkyl)$_2$, alkoxy, alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Preferred examples are furanyl, imidazyl, pyranyl, pyrrolyl, and pyridyl.

General Discussion

Embodiments of the present disclosure provide for a triptycene-based A-B monomer, a method of making a triptycene-based A-B monomer, a triptycene-based ladder polymer, a method of making a triptycene-based ladder polymers, a method of using triptycene-based ladder polymers, a structure incorporating triptycene-based ladder polymers, a method of gas separation, and the like.

In an embodiment, the triptycene-based A-B monomer has the significant advantage in step-growth polymerization over the AA-BB monomers used previously in that a high molecular weight can be achieved without strict control over stoichiometric balance, as required for AA-BB polycondensation. In other words, the process for making the triptycene-based ladder polymer using the triptycene-based A-B monomer allows attainment of high molecular weight triptycene-based ladder polymers without strict control over stoichiometric balance, simplifying the synthetic process. Moreover, the triptycene-based A-B monomer contains a site of contortion created by a triptycene moiety that is different from the traditionally employed spiro center (i.e., PIM-1) and which, by virtue of its rigid three-dimensional framework, is an attractive building block for microporous organic materials.

In addition, embodiments of the triptycene-based A-B monomer and triptycene-based ladder polymer are expected to be economically attractive compared with the current polymer-based membranes due to their high permeabilities and excellent selectivities. Higher permeability offers savings in capital cost of membrane systems by reducing area requirements to handle a given process flow. It also reduces energy consumption by reducing compression requirements. Higher selectivity introduces large savings by reducing cross-over of valuable gas feed components into the permeate streams and also by reducing the need for multi-stage systems.

Embodiments of the triptycene-based ladder polymer have one or more of the following characteristics: intrinsic microporosity, good thermal stability, and enhanced solubility in common organic solvents. An intrinsically microporous polymer is defined herein as a polymeric material with pore sizes of less than 2 nm and a surface area of >100 m$^2$/g, as determined by nitrogen adsorption at 77 K. Triptycene-based ladder polymers are microporous and have high BET surface area, up to 800 m$^2$/g as conventionally measured by the area accessible to N$_2$ molecules at 77K. Although not intending to be bound by theory, this microporosity appears to have resulted from the incorporation of the rigid three-dimensional structure of a triptycene moiety, which prevents close packing of the polymer chains and decreases the interchain interactions. Example 1 includes exemplary reaction schemes and gas separation data for embodiments of triptycene-based ladder polymer.

In an exemplary embodiment, a triptycene-based ladder polymer can be used to form a gas separation membrane. The membrane can have an exceptional performance for gas separation applications significantly transcending the upper bounds for a wide variety of applications. Specifically, embodiments of membranes incorporating the triptycene-based ladder polymer provide unprecedented performance in gas separation applications including molecular sieving applications like air separation and hydrogen recovery from ammonia purge-gas streams. In an embodiment, the membrane can be about 1 mm thick and have a diameter (or length and width) of about 1 mm to 1 m or about 10 cm to 100 cm.

In an exemplary embodiment, triptycene-based ladder polymers are soluble in common organic solvents and can readily be cast into robust films. A representative triptycene-based ladder polymer, 9,10-di-isopropyl-substituted ladder polymer (TPIM-1) was tested for gas transport properties using a constant-volume, variable pressure apparatus with pure-gas feeds at 2 bar feed pressure and 25° C. Unprecedented gas separation performance was observed for molecular sieving applications like air separation (O$_2$/N$_2$, for oxygen or nitrogen enrichment) and hydrogen recovery (H$_2$/N$_2$, H$_2$/CH$_4$, from ammonia purge gas streams), with performance far transcending the latest upper bounds. The polymer also demonstrated outstanding performance in natural gas sweetening (CO$_2$/CH$_4$, removal of acid gas) which is one of the fastest growing applications of membrane technology today. Example 1 includes comparative examples representing the current state-of-the-art in gas separation performance for this class of polymers (i.e., PIM-1, PIM-7, PIM-SBF).

In addition, due to their good solubilities, thermal and chemical stabilities, and high microporosities, these materials can be implemented in a wide range of industrial applications related to adsorption, heterogeneous catalysis, low dielectric constant films, sensors, and gas storage.

Embodiments of the triptycene-based A-B monomer and triptycene-based ladder polymer include both catechol (A) and aromatic ortho-difluoride (B) functionalities. In an exemplary embodiment, the triptycene-based ladder polymer can be made using a triptycene-based A-B monomer as shown in the following structure:

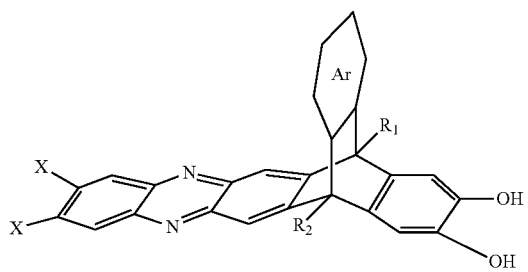

In an embodiment, X can be a halogen such as F or Cl. In an embodiment, Ar can be a substituted or un-substituted aromatic moiety such as a substituted or un-substituted aryl group, or a substituted or un-substituted heteroaryl group. In an embodiment, Ar can be a substituted or un-substituted phenyl group. In an embodiment, Ar can be selected from:

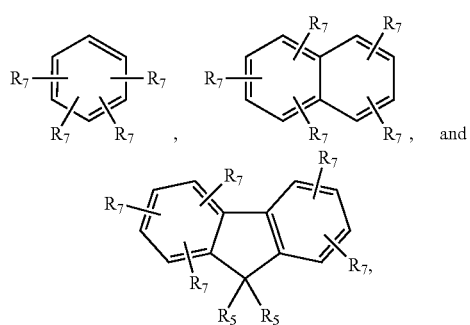

that is bonded by removing a hydrogen from the ring for two carbons and each ring can have up to four $R_7$ groups. In an embodiment, Ar can be selected from

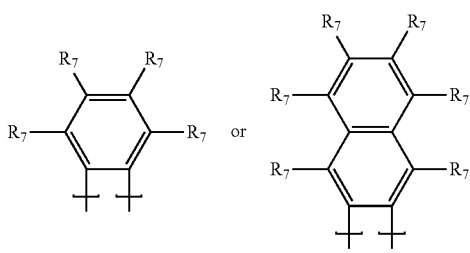

In an embodiment, each $R_5$ and $R_7$ can be independently a linear or branched, substituted or un-substituted, alkyl group (e.g., methyl group). Each $R_5$ can be independently selected. Each $R_7$ can be independently selected.

In an embodiment, R1 and R2 can each independently be hydrogen or a linear or branched, substituted or non-substituted alkyl group, a substituted or un-substituted aryl group, or a substituted or un-substituted heteroaryl group. In particular, R1 and R2 can each be independently a substituted or un-substituted, linear or branched alkyl group.

Representative triptycene-based A-B monomers can have the following structures:

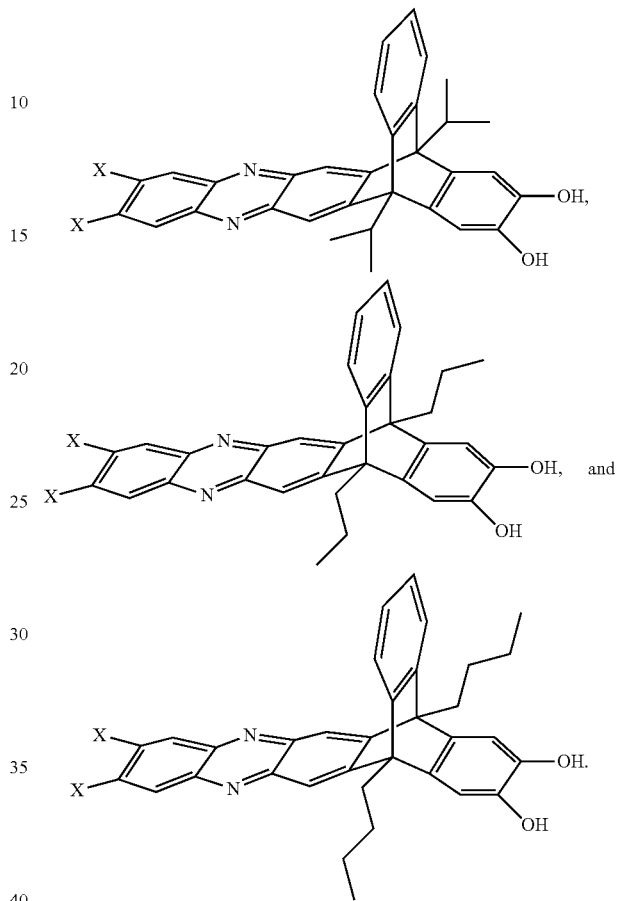

In an exemplary embodiment, the triptycene-based A-B monomer can be synthesized using the synthesis described in Scheme 1 in Example 1. Although exemplary specific solvent, acids, and other reagents are described, other suitable solvent, acids, and reagents can be used if they accomplish the same purpose.

In an exemplary embodiment, the triptycene-based ladder polymer can include a compound as represented by the following structure:

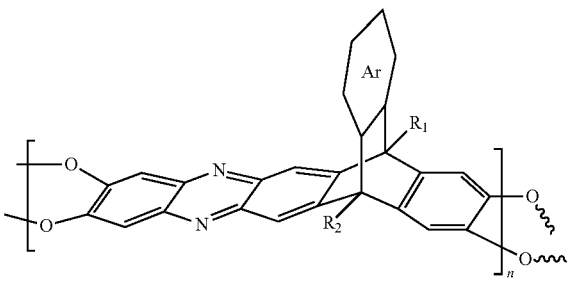

In an embodiment, n can be 1 to 10,000 or more. In an embodiment, X can be a halogen such as F or Cl. In an embodiment, Ar can be a substituted or un-substituted aromatic moiety such as a substituted or un-substituted aryl group, or a substituted or un-substituted heteroaryl group, and those described in reference to Ar herein. In an embodiment, Ar can be a substituted or un-substituted phenyl group.

In an embodiment, R1 and R2 can each independently be hydrogen or a substituted or non-substituted alkyl group, a substituted or un-substituted aryl group, or a substituted or un-substituted heteroaryl group. In particular, R1 and R2 can each be independently a substituted or un-substituted, linear or branched alkyl group.

Representative triptycene-based ladder polymers can have the following structures:

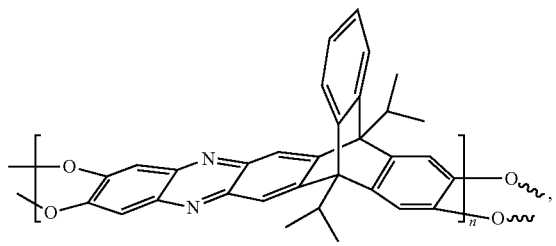

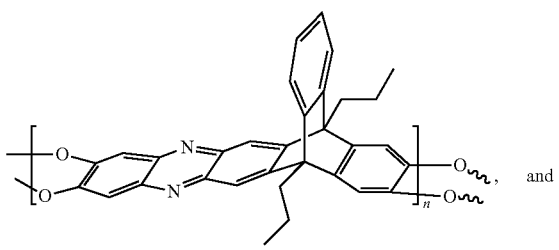

and

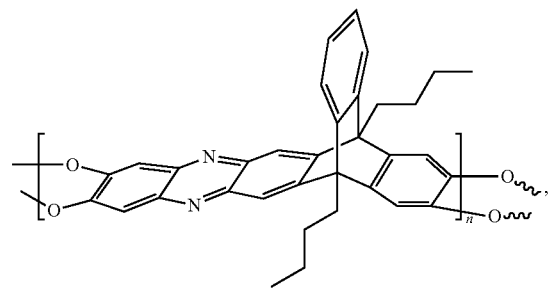

In an exemplary embodiment, the triptycene-based ladder polymer can be synthesized by a self-polycondensation reaction of the triptycene-based A-B monomer. In an embodiment, the self-polycondensation reaction can be illustrated as shown below:

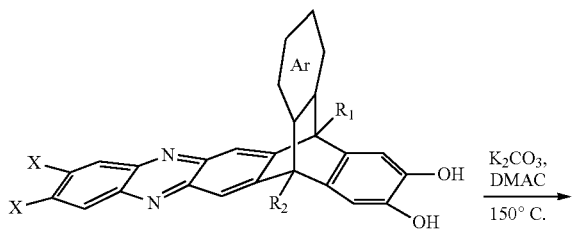

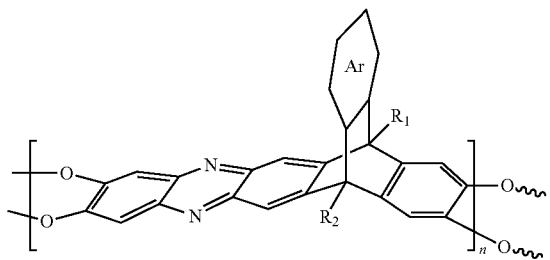

Although exemplary specific solvents, acids, and other reagents are described, other suitable solvent, acids, and reagents can be used if they accomplish the same purpose.

As mentioned above, triptycene-based ladder polymers of the present disclosure can be used to form membranes that can be used in gas separation. The membranes including the triptycene-based ladder polymers can be formed using conventional techniques.

As mentioned above, the membranes of the present disclosure can be used in conventional gas separation systems such as systems to enrich a specific gas in a gas mixture (e.g., oxygen enrichment, nitrogen enrichment, and the like). In addition, the membranes can be used in hydrogen gas separations.

In general, a first gas is separated from a first gas mixture with a membrane of the present disclosure to form a second gas mixture that is enriched in one or more components of the first gas mixture. In an embodiment, the result can be the separation of a gas(es) from another gas(es) such as in oxygen/nitrogen, hydrogen/methane, hydrogen/nitrogen, carbon dioxide/methane, carbon dioxide/nitrogen, hydrogen/$C_2+$ hydrocarbons, hydrogen sulfide/methane, carbon dioxide/hydrogen sulfide, ethylene/ethane, propylene/propane, water vapor/hydrocarbons, $C_2+$/hydrogen, $C_2+$/methane, and the like.

EXAMPLES

Now having described the embodiments of the disclosure, in general, the examples describe some additional embodiments. While embodiments of the present disclosure are described in connection with the example and the corresponding text, there is no intent to limit embodiments of the disclosure to these descriptions. On the contrary, the intent is to cover all alternatives, modifications, and equivalents included within the spirit and scope of embodiments of the present disclosure.

Example 1

Scheme (1): Synthetic route to A-B monomers

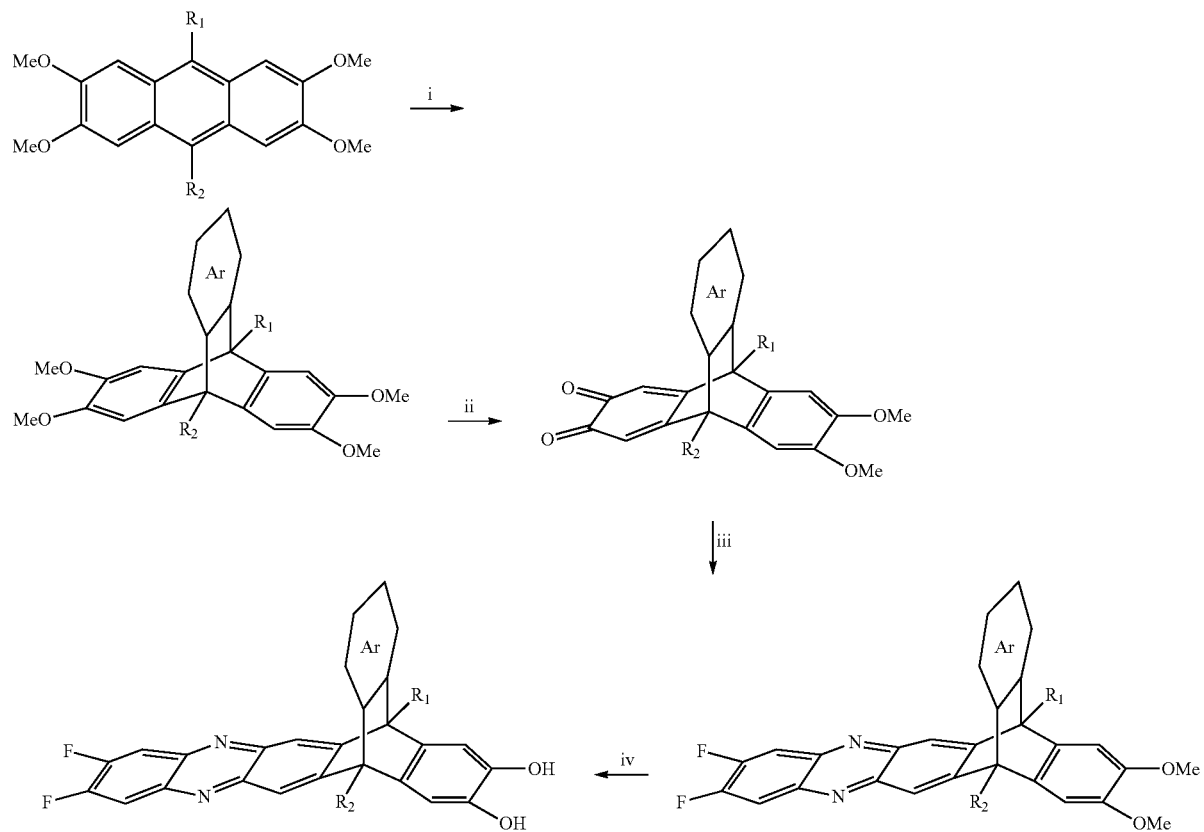

Scheme 1. Synthetic route to 9,10-dialkyl triptycene-based A-B monomers. Reagents and conditions: (i) diazonium salt of Anthranilic acid or substituted anthranilic acid, 1,2-epoxypropane, $CH_2Cl_2$, reflux; (ii) 0.25 M $HNO_3$, AcOH and $CH_2Cl_2$ (1:1, v:v), 5 minutes; (iii) 4,5-difluoro-1,2-diaminobenzene, ethanol, reflux, 6 h; (iv) $BBr_3$, $CH_2Cl_2$, 2 h.

Where Ar is a substituted or un-substituted aromatic moiety and, $R_1$ and $R_2$ are aryl, alkyl groups ($R_1$=$R_2$ or $R_1 \neq R_2$) halogen or hydrogens.

Scheme (2): Synthetic route to novel ladder polymers

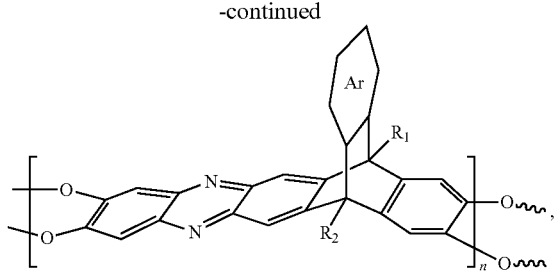

Scheme 2: Self-polymerizatioin of the A-B monomers to form ladder polymers of intrinsic microporosity.

Specific examples of ladder polymers prepared from 9,10-disubstituted A-B monomers:

TPIM-1

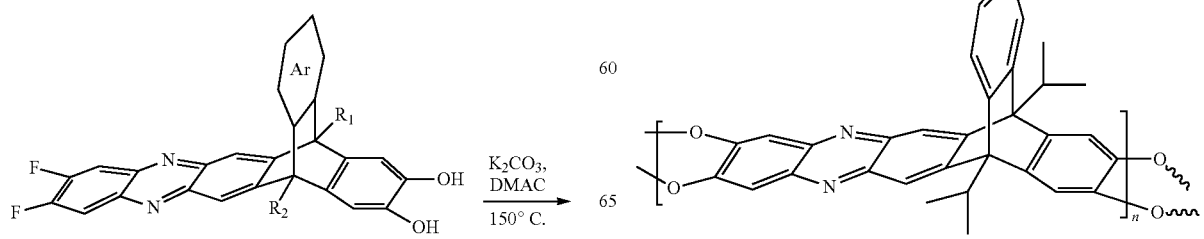

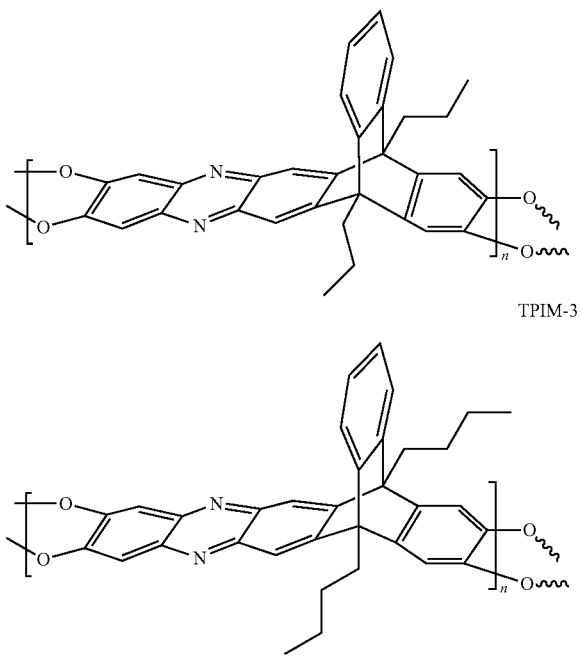

Gas Transport Testing Method:

The gas permeability of the membranes was determined using the constant-volume/variable-pressure method. The membranes were degassed in the permeation test apparatus on both sides under high vacuum at 25° C. for at least 24 h. The increase in permeate pressure with time was measured by a MKS Baratron transducer (range from 0 to 10 torr). The permeability of all gases was measured at 2 bar and 25° C. and was calculated by:

$$P = 10^{10} \frac{V_d l}{p_{up} TRA} \frac{dp}{dt}$$

where P is the permeability (Barrers) (1 Barrer=$10^{-10}$ cm$^3$ (STP) cm/(cm$^2$ s cmHg)), $p_{up}$ is the upstream pressure (cmHg), dp/dt is the steady-state permeate-side pressure increase (cmHg/s), $V_d$ is the calibrated permeate volume (cm$^3$), l is the membrane thickness (cm), A is the effective membrane area (cm$^2$), T is the operating temperature (K), and R is the gas constant (0.278 cm$^3$ cmHg/(cm$^3$ (STP) K)). The pure-gas selectivity of gas A over gas B was calculated by the ratio of their permeabilities:

$$\alpha_B^A = P_A/P_B$$

Tabulation of Data on Permeability/Selectivity

| Polymer | Permeability O$_2$ (Barrer) | α (O$_2$/N$_2$) | Reference |
|---|---|---|---|
| PIM-7 | 190 | 4.5 | [1] |
| PIM-1 (a) | 1300 | 3.8 | [2] |
| PIM-1 (b) | 786 | 3.3 | [3] |
| PIM-SBF | 2640 | 3.4 | [4] |
| TPIM-1 | 368 | 6.8 | [This example] |
| TPIM-2 | 101 | 5.7 | [This example] |
| TPIM-3 | 76 | 4.6 | [This example] |

H$_2$/N$_2$

| Polymer | Permeability H$_2$ (Barrer) | α (H$_2$/N$_2$) | Reference |
|---|---|---|---|
| PIM-7 | 860 | 20.5 | [1] |
| PIM-1 (a) | 3600 | 11.0 | [2] |
| PIM-1 (b) | 2332 | 9.8 | [3] |
| PIM-SBF | 6320 | 8.1 | [4] |
| TPIM-1 | 2666 | 49 | [This example] |
| TPIM-2 | 655 | 37 | [This example] |
| TPIM-3 | 379 | 23 | [This example] |

CO$_2$/CH$_4$

| Polymer | Permeability CO$_2$ (Barrer) | α (CO$_2$/CH$_4$) | Reference |
|---|---|---|---|
| PIM-7 | 1100 | 17.7 | [1] |
| PIM-1 (a) | 6500 | 15.0 | [2] |
| PIM-SBF | 13900 | 12.6 | [4] |
| TPIM-1 | 1549 | 33 | [This example] |
| TPIM-2 | 434 | 24 | [This example] |
| TPIM-3 | 384 | 17 | [This example] |

Gas Transport Properties of Structurally-Related PIMs

| Gas | TPIM-1 | TPIM-2 | TPIM-3 |
|---|---|---|---|
| | Permeability (25° C., 2 bar) (Barrer: 1 Barrer = $10^{-10}$ cm$^3$(STP) cm s$^{-1}$ cm$^{-2}$ cmHg$^{-1}$) | | |
| He | — | 324 | 194 |
| H$_2$ | 2666 | 655 | 379 |
| N$_2$ | 54 | 18 | 17 |
| O$_2$ | 368 | 101 | 76 |
| CH$_4$ | 47 | 18 | 22 |
| CO$_2$ | 1549 | 434 | 384 |
| Gas Pair | Ideal Selectivity | | |
| O$_2$/N$_2$ | 6.8 | 5.7 | 4.6 |
| H$_2$/N$_2$ | 49 | 37 | 23 |
| CO$_2$/CH$_4$ | 33 | 24 | 17 |

REFERENCES

1. P. M. Budd, K. J. Msayib, C. E. Tattershall, B. S. Ghanem, K. J. Reynolds, N. B. McKeown, and D. Fritsch, 'Gas Separation Membranes from Polymers of Intrinsic Microporosity', *Journal of Membrane Science*, 251 (2005), 263-269.
2. S. Thomas, I. Pinnau, N. Y. Du, and M. D. Guiver, 'Pure- and Mixed-Gas Permeation Properties of a Microporous Spirobisindane-Based Ladder Polymer (Pim-1)', *Journal of Membrane Science*, 333 (2009), 125-131.
3. C. L. Staiger, S. J. Pas, A. J. Hill, and C. J. Cornelius, 'Gas Separation, Free Volume Distribution, and Physical Aging of a Highly Microporous Spirobisindane Polymer', *Chemistry of Materials*, 20 (2008), 2606-2608.
4. C. G. Bezzu, M. Carta, A. Tonkins, J. C. Jansen, P. Bernardo, F. Bazzarelli, and N. B. McKeown, 'A Spirobifluorene-Based Polymer of Intrinsic Microporosity with Improved Performance for Gas Separation', *Advanced Materials*, 24 (2012), 5930.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A composition, comprising:
a triptycene-based ladder polymer having the following structure:

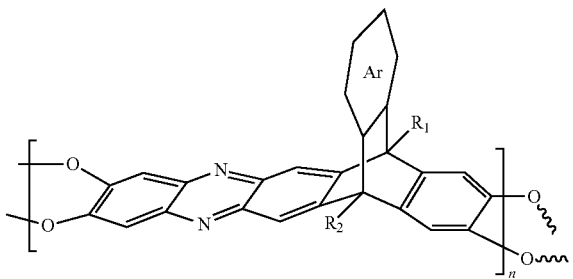

wherein n is 1 to 10,000, wherein Ar is a substituted or un-substituted aromatic moiety, wherein each of R1 and R2 is independently selected from the group consisting of: hydrogen, a halogen, a substituted or un-substituted, branched or linear methyl, ethyl, or propyl group, a substituted or un-substituted aryl group, a substituted or un-substituted heteroaryl group, and a substituted or un-substituted phenyl group.

2. The composition of claim 1, wherein the substituted or un-substituted aromatic moiety is selected from the group consisting of: a substituted or un-substituted aryl group and a substituted or un-substituted heteroaryl group.

3. The composition of claim 1, wherein the substituted or un-substituted aromatic moiety is selected from the group consisting of: a substituted or un-substituted phenyl group and each of R1 and R2 are independently a propyl or isopropyl group.

4. The composition of claim 1, wherein the triptycene-based ladder polymer has the following structure:

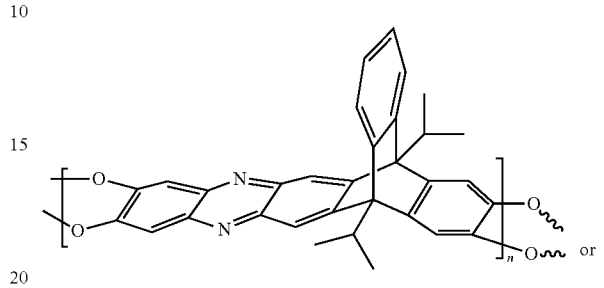

or

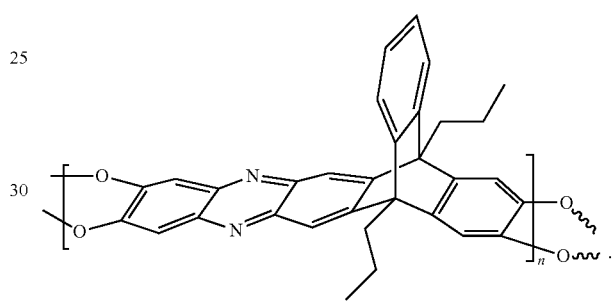

5. A composition, comprising: a monomer described by the following structure:

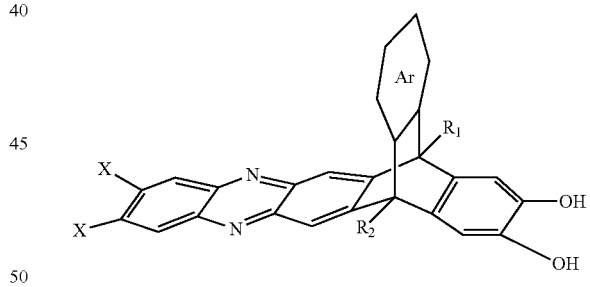

wherein Ar is a substituted or un-substituted aromatic moiety, wherein each of R1 and R2 is independently selected from the group consisting of: hydrogen, a substituted or un-substituted, linear or branched methyl, ethyl, or propyl group, a substituted or un-substituted aryl group, a substituted or un-substituted heteroaryl group, and substituted or un-substituted phenyl group, and wherein X is fluorine.

6. The composition of claim 5, wherein the substituted or un-substituted aromatic moiety is selected from the group consisting of: a substituted or un-substituted phenyl group.

7. The composition of claim 5, wherein each of $R_1$ and $R_2$ are independently a propyl or isopropyl group.

8. A membrane, comprising: a polymer including a triptycene-based ladder polymer having the following structure:

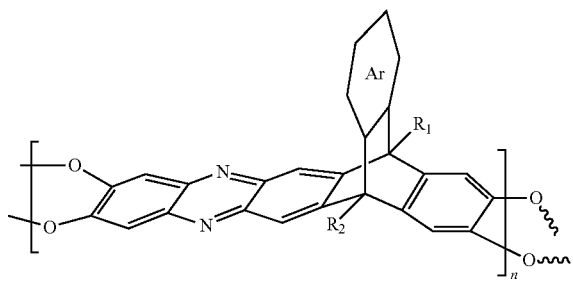

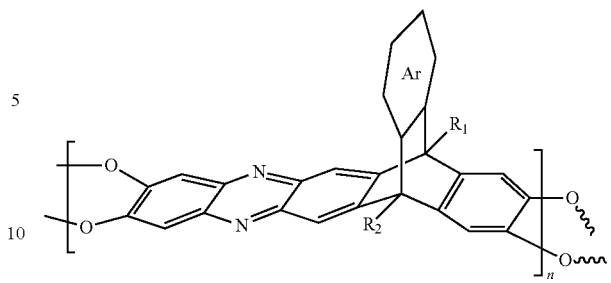

wherein n is 1 to 10,000, wherein Ar is a substituted or un-substituted aromatic moiety, wherein each of R1 and R2 is independently selected from the group consisting of: hydrogen, a halogen, a substituted or un-substituted, branched or linear methyl, ethyl, or propyl group, a substituted or un-substituted aryl group, a substituted or un-substituted heteroaryl group, and a substituted or un-substituted phenyl group.

9. The membrane of claim 8, wherein the substituted or un-substituted aromatic moiety is selected from the group consisting of: a substituted or un-substituted phenyl group.

10. The membrane of claim 8, wherein each of $R_1$ and $R_2$ are independently a methyl, ethyl, propyl or isopropyl group.

11. A method of separating a gas from a gas mixture, comprising: separating a first gas from a first gas mixture with a membrane to form a second gas mixture, wherein the membrane includes a polymer including a triptycene-based ladder polymer having the following structure:

wherein n is 1 to 10,000, wherein Ar is a substituted or un-substituted aromatic moiety, wherein each of R1 and R2 is independently selected from the group consisting of: hydrogen, a halogen, a substituted or un-substituted, branched or linear methyl, ethyl, or propyl group, a substituted or un-substituted aryl group, a substituted or un-substituted heteroaryl group, and a substituted or un-substituted phenyl group.

12. The method of claim 11, wherein the first gas is selected from the group consisting of: He, $H_2$, $CO_2$, $H_2S$, $O_2$, $N_2$, $CH_4$, saturated $C_2+$ hydrocarbons, $C_2H_4$, $C_2H_6$, $C_3H_6$, $C_3H_8$ and a combination thereof.

13. The method of claim 11, wherein the second gas mixture is oxygen enriched, nitrogen enriched, $H_2$ enriched, methane enriched, $C_2+$ hydrocarbons enriched, ethylene enriched, propylene enriched, or $CO_2$ enriched when compared to the first gas mixture.

* * * * *